(12) United States Patent
Chou et al.

(10) Patent No.: US 8,134,357 B2
(45) Date of Patent: Mar. 13, 2012

(54) MULTI-ELECTRODE MEASURING SYSTEM

(75) Inventors: Jung-Chuan Chou, Yunlin County (TW); Wei-Chuan Chen, Pingtung County (TW); Cheng-Wei Chen, Pingtung County (TW); Chien-Cheng Chen, Taichung County (TW)

(73) Assignee: National Yunlin University of Science and Technology, Yunlin (TW)

( * ) Notice: Subject to any disclaimer, the term of this patent is extended or adjusted under 35 U.S.C. 154(b) by 18 days.

(21) Appl. No.: 12/777,942

(22) Filed: May 11, 2010

(65) Prior Publication Data

US 2011/0115473 A1    May 19, 2011

(30) Foreign Application Priority Data

Nov. 16, 2009    (TW) ................. 98138785 A

(51) Int. Cl.
*G01R 13/00*    (2006.01)

(52) U.S. Cl. ............... 324/140 R; 324/425; 324/439
(58) Field of Classification Search ........... 324/140 R, 324/425–450
See application file for complete search history.

Primary Examiner — Arleen M Vazquez

(57) ABSTRACT

The invention provides a multi-electrode measuring system including a front end device which is a sensing device including a multi-electrode sensing device having a plurality of electrodes; a multi-channel fixture coupled to the multi-electrode sensing device; and a reference electrode. A back-end device as a virtual instrumentation is an electronic device including a read out circuit device coupled to the multi-channel fixture and the reference electrode for receiving each original signal from each electrode of the multi-electrode sensing device and the reference electrode determining a sample solution; a data acquisition device coupled to the read out circuit device for digitizing each original signal to form a digital signal and for array sampling; and a signal processing device coupled to the data acquisition device for processing each signal.

43 Claims, 14 Drawing Sheets

MULTI-ELECTRODE MEASURING SYSTEM

CROSS REFERENCE TO RELATED APPLICATIONS

This Application claims priority of Taiwan Patent Application No. 098138785, filed on Nov. 16, 2009, the entirety of which is incorporated by reference herein.

BACKGROUND OF THE INVENTION

1. Field of the Invention

The present invention relates to an ion measuring system, and in particular relates to a multi-electrode measuring system which is able apply for biomedicine, chemistry related fields, etc.

2. Description of the Related Art

The ion sensitive field effect transistor (ISFET) was first invented by P. Bergveld in 1970, and the ISFET is based on a metal-oxide-semiconductor field effect transistor (MOSFET). Moreover, the gate of the MOSFET was replaced by a sensing membrane and electrolyte. A sensing membrane and $H^+$ and $OH^-$ in a sample solution results in an adsorption-binding effect to make the potential on the surface of an electrode change, thus obtaining the ion concentration of a sample solution.

In 1983, J. Van der Spiegel et al developed an extended gate chemical sensitive field effect transistor, which used a plane array structure, including four sensing parts deposited of different materials such as $IrO_x$, $LaF_3$, $AgCl$ and $Ag_2S$ to from the sensing thin films for detecting four kinds of ions, $H^+$, $F^-$, $Cl^-$ and $Ag^+$, (J. Van der Spiegel, I. Lauks, P. Chan D. Babic, 1983, "The extended gate chemical sensitive field effect transistor as multi-species microprobe", Sensors and Actuators B, Vol. 4, pp. 291-298).

Taiwan Patent No. I236533, disclose a biochemical sensing method and the sensing device thereof. A current/voltage converting circuit is able to convert current signals into analog voltage signals; and the analog voltage signals may be converted into digital voltage signals by an analog/digital converter; finally an electronic device is used to receive and analyze the digital voltage signals and an amount of a specific compound is determined by the analyzing step.

U.S. Pat. No. 7,348,783 disclose a multi-functional pH meter and the fabrication thereof. The pH meter provides an immediate display of the measurement result and a saving function which is beneficial for development of a portable detecting device. In addition, the multi-functional pH meter has data communication functionality with a computer, drift and hysteresis software calibration is also provided.

BRIEF SUMMARY OF THE INVENTION

The invention provides a multi-electrode measuring system, comprising a front end device which is a sensing device comprising: a multi-electrode sensing device having a plurality of electrodes; a multi-channel fixture coupled to the multi-electrode sensing device; and a reference electrode. A back-end device as a virtual instrumentation is an electronic device comprising: a read out circuit device coupled to the multi-channel fixture and the reference electrode for receiving each original signal from each electrode of the multi-electrode sensing device and the reference electrode determining a sample solution; a data acquisition device coupled to the read out circuit device for digitizing each original signal to form a digital signal and for array sampling; and a signal processing device coupled to the data acquisition device for processing each digital signal. Frameworks for the signal processing device processing each the digital signal comprise: an acquisition framework for dynamically receiving data of the array sampling of the digital signal of each electrode from the data acquisition device; a digital filter framework for calculating a series of the data of the array sampling from each electrode obtained from the acquisition framework to from a group of estimated direct current values; a display framework for immediately displaying the group of estimated direct current values on a display; a storage framework for immediately saving the group of estimated direct current values in a memory unit; and an analysis framework for calculating the group of estimated direct current values converged therein via the storage framework by a particular algorithm.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein:

FIG. 2b shows a side view of one independent electrode sensor of the non-flexible multi-electrode sensing device in FIG. 2a;

FIG. 3b shows a side view of the electrode sensor of the non-flexible multi-electrode sensing device in FIG. 3a;

FIG. 4b shows a disassembly view of one independent electrode sensor of the flexible multi-electrode sensing device in FIG. 4a;

FIG. 4c shows a top view of one electrode sensor of the flexible multi-electrode sensing device in FIG. 4a;

FIG. 5b shows a disassembly view of the flexible multi-electrode sensing device in FIG. 5a;

FIG. 5c shows a top view of the flexible multi-electrode sensing device in FIG. 5a;

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The main structure of the multi-electrode measuring system of the invention comprises a sensing device and an electronic device, and in the electronic device, a real instrumentation is replaced by a virtual instrumentation. The multi-electrode measuring system of the invention will be detailed in the following.

Figure 1:
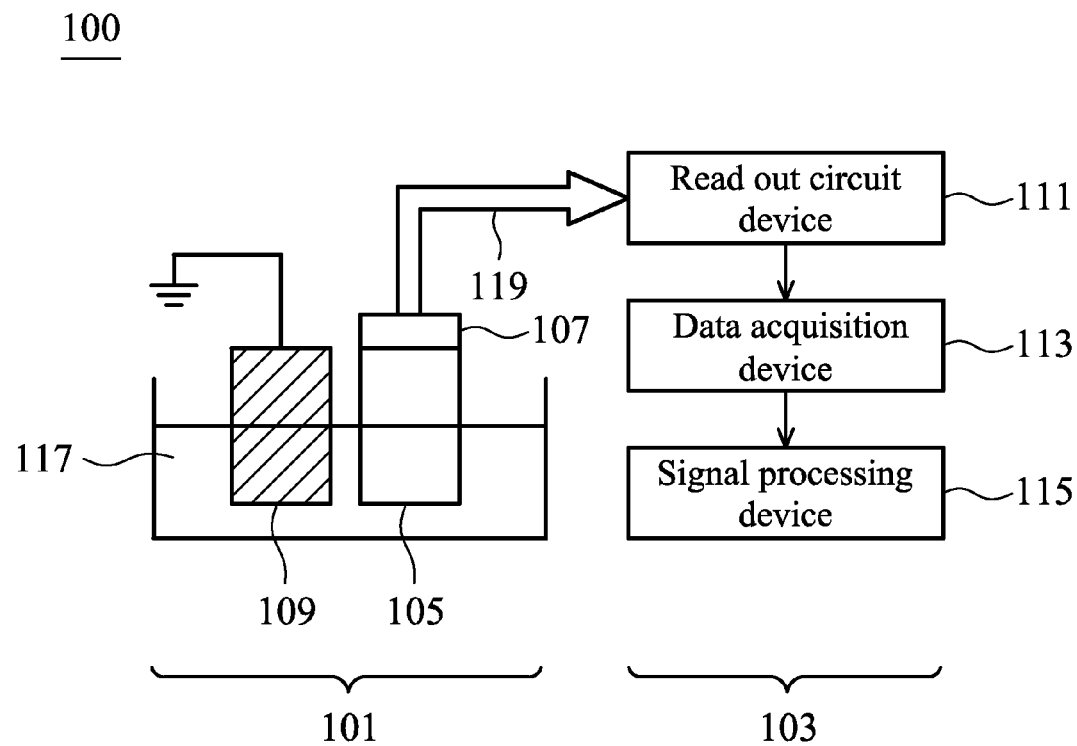
FIG. 1 shows an embodiment of the multi-electrode measuring system of the invention.

See FIG. 1. FIG. 1 shows an embodiment of the multi-electrode measuring system of the invention 100. The multi-electrode measuring system 100 may comprise a front-end device 101 and a back-end device 103.

The front-end device 101 is a sensing device, which may comprise a multi-electrode sensing device 105, a multi-channel fixture 107 and a reference electrode 109. The multi-channel fixture 107 is coupled to the multi-electrode sensing device 105. The multi-electrode sensing device 105 comprises a plurality of electrodes, and may comprise a non-flexible multi-electrode sensing device or a flexible multi-electrode sensing device. The multi-channel fixture 107 may comprise a multiple pin connector, such as DuPont connector 2.54. The reference electrode 109 provides ground electric potential for a sample solution, and may comprise an Ag/AgCl reference electrode.

Figure 2A:
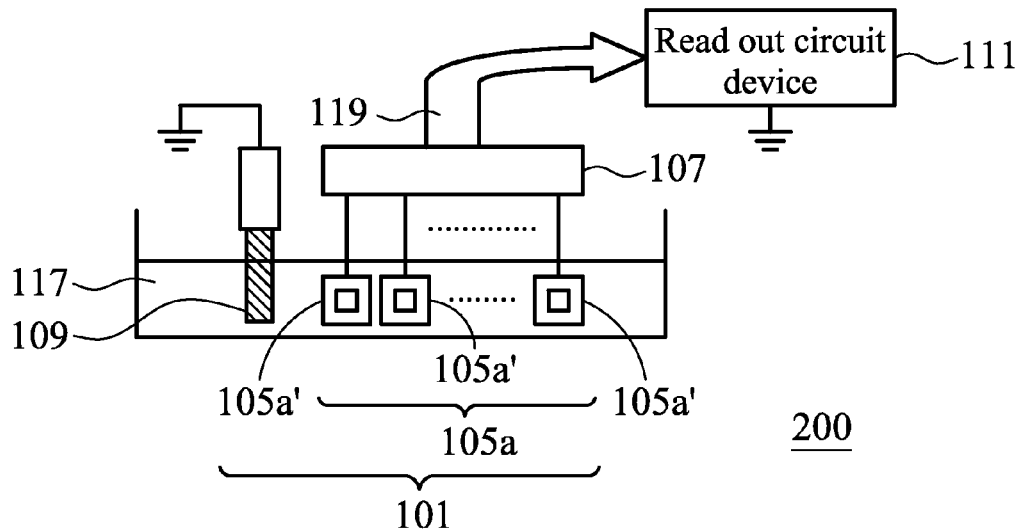
FIG. 2a shows an embodiment of the multi-electrode measuring system of the invention.
Figure 2B:
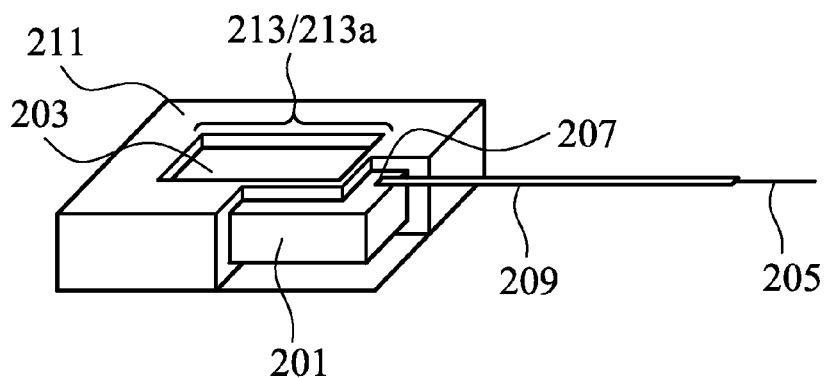

FIG. 2a shows an embodiment of the multi-electrode measuring system of the invention 200. The multi-electrode measuring system 200 has one embodiment of a non-flexible multi-electrode sensing device 105a. In FIG. 2a, the non-flexible multi-electrode sensing device 105 comprises a plurality of independent electrode sensors 105a'. FIG. 2b shows a side view of one independent electrode sensor 105a' in FIG. 2a. The independent electrode sensor 105a' may comprise a non-flexible substrate 201, a sensing membrane 203 and a conductive wire 205 extended from the sensing membrane 203, wherein the conductive wire 205 connects to the multi-channel fixture 107. The non-flexible substrate 201 may comprise a silicon substrate. The sensing membrane 203 is on the non-flexible substrate 201, and may comprise a ruthenium dioxide sensing membrane. The ruthenium dioxide sensing membrane may be deposited on the non-flexible substrate 201 by a radio frequency sputtering system. A material of the conductive wire 205 may comprise copper, and the conductive wire 205 may be connected to the sensing membrane 203 by a sliver paste layer 207. In one embodiment a plastic shell 209 may be used for covering the conductive wire 205.

In another embodiment, the independent electrode sensor 105a' may further comprise an insulating package layer 211 for packing the non-flexible substrate 201 and the sensing membrane 203, wherein the insulating package layer 211 has an opening 213 for exposing a part of the sensing membrane 203, which forms a sensing window 213a. A material of the insulating package layer 211 may comprise epoxy resin.

Figure 3A:
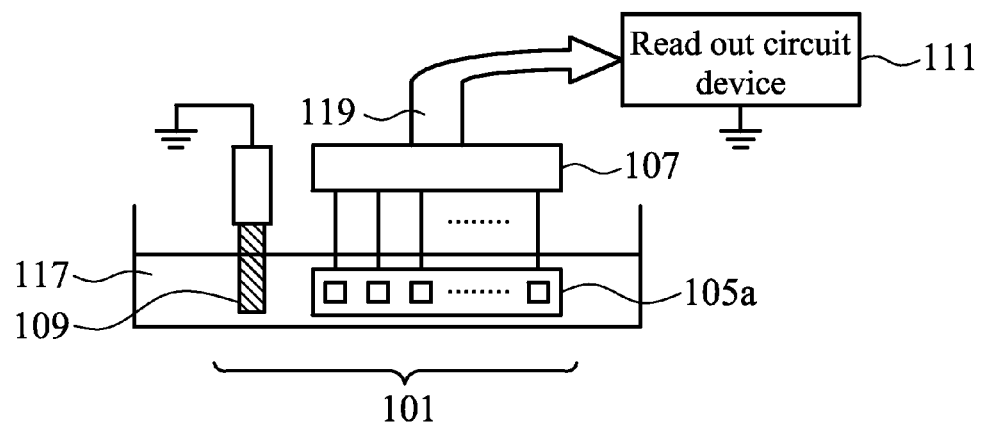
FIG. 3a shows an embodiment of the multi-electrode measuring system of the invention.
Figure 3B:
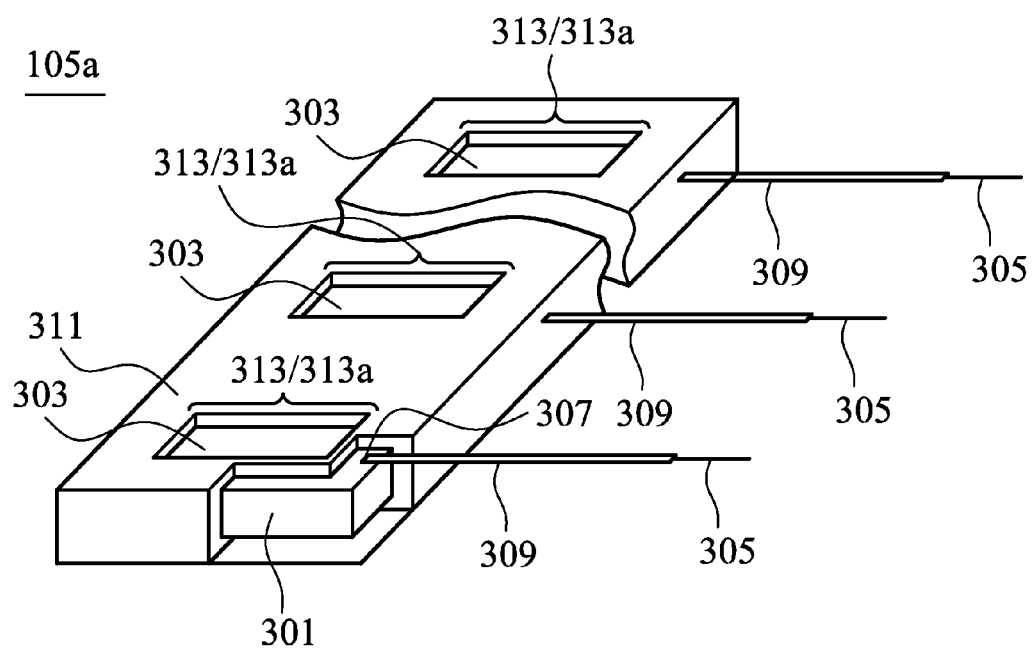

FIG. 3a shows an embodiment of the multi-electrode measuring system of the invention 300. The multi-electrode measuring system 300 has another embodiment of a non-flexible multi-electrode sensing device 105a. FIG. 3b shows a side view of the non-flexible multi-electrode sensing device 105a in FIG. 3a. The non-flexible multi-electrode sensing device 105a may comprise a non-flexible substrate 301, a plurality of sensing membranes 303 and a plurality of conductive wires 305 extended from the plurality of sensing membranes 303, wherein the plurality of conductive wires 305 connects to the multi-channel fixture 107, respectively. The non-flexible substrate 301 may comprise a silicon substrate. The plurality of sensing membranes 303 are on the non-flexible substrate 301, and may comprise a plurality of ruthenium dioxide sensing membranes. The ruthenium dioxide sensing membrane may be deposited on the non-flexible substrate 301 by a radio frequency sputtering system. A material of the conductive wire 305 may comprise copper, and the conductive wire 305 may be connected to the sensing membrane 303 by a sliver paste layer 307. In one embodiment a plastic shell 309 may be used for covering the conductive wire 305.

In another embodiment, the non-flexible multi-electrode sensing device 105a may further comprise an insulating package layer 311 for packing the non-flexible substrate 301 and the plurality of sensing membranes 303, wherein the insulating package layer 311 has a plurality of openings 313 for exposing a part of each of the plurality of sensing membranes 303, respectively, which forms a plurality of sensing windows 313a. A material of the insulating package layer 311 may comprise epoxy resin.

In one embodiment, the related parameters for forming the ruthenium dioxide sensing membrane with the radio frequency sputtering system mentioned above are set as follow: (1) Power of radio frequency sputtering: 100 W; (2) Frequency of radio frequency sputtering: 13.56 MHz; (3) Pressure: 10 mTorr; (4) Target purity of Ru: 99.99%; (5) Gas flow rate ($Ar:O_2$): 40:20 (in sccm); (6) Sputtering time: 15 minutes; (7) Thickness: 350 nm.

Moreover, the insulating package layer is used for isolating the chemical and electronic interference in the environment (solution). In one embodiment, epoxy resin is used as an insulating package layer for packing the non-flexible substrate and the sensing membrane, has a 2 mm×2 mm opening on the sensing membrane to form a sensing window, and then placed in a oven to solidify. The temperature of the oven is about 120-140° C. and the treatment time is about 30-60 minutes.

Figure 4A:
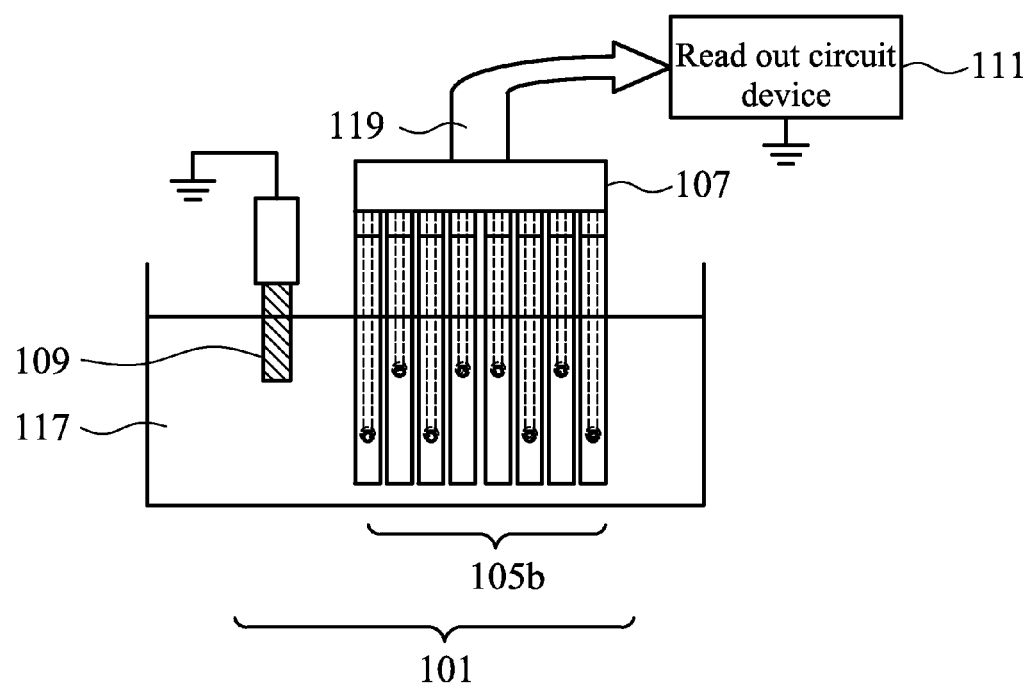
FIG. 4a shows an embodiment of the multi-electrode measuring system of the invention.
Figure 4B:
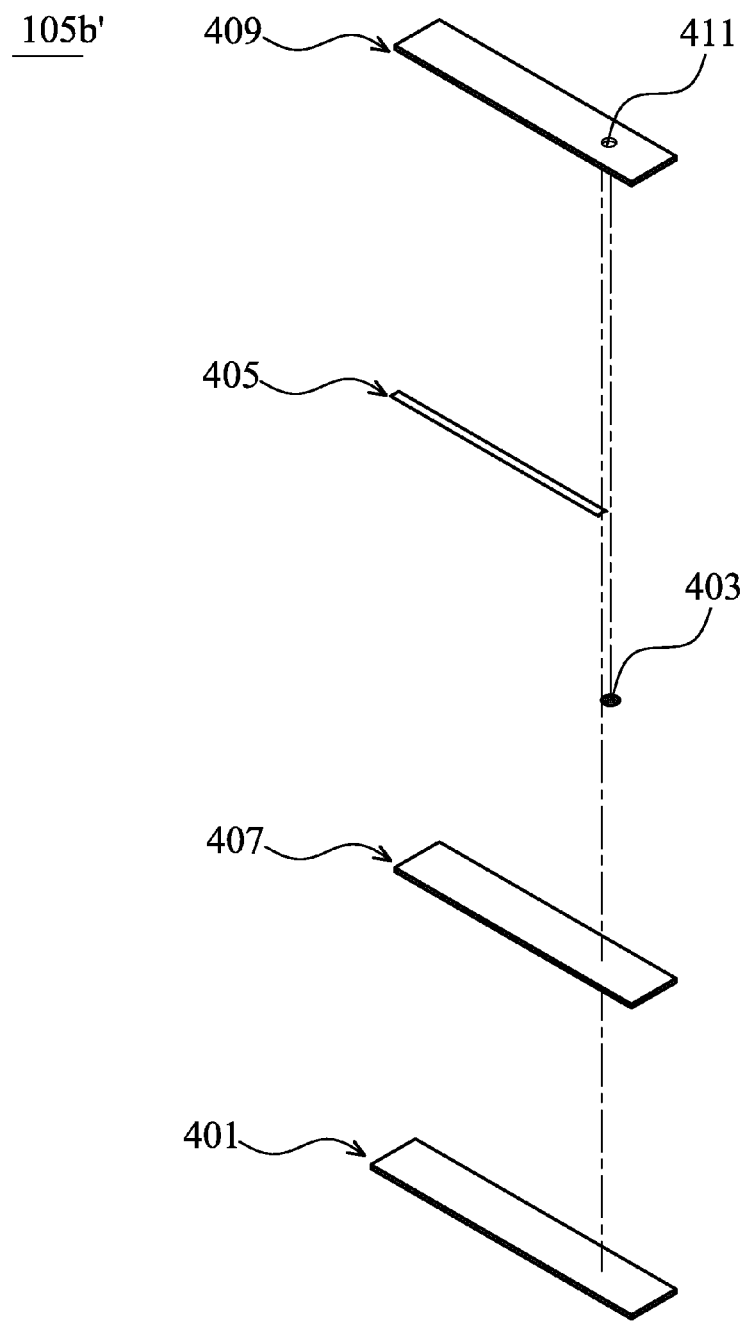
Figure 4C:
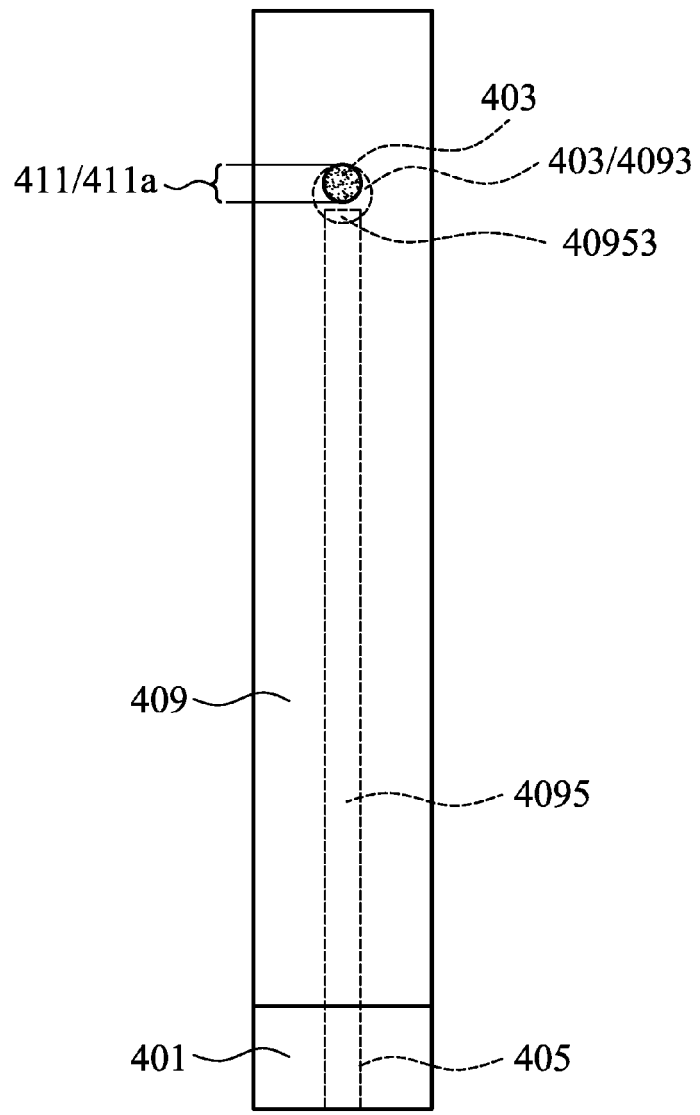

FIG. 4a shows an embodiment of the multi-electrode measuring system of the invention 400. The multi-electrode measuring system 400 has one embodiment of a flexible multi-electrode sensing device 105b. In FIG. 4a, the flexible multi-electrode sensing device 105b comprises a plurality of independent electrode sensors 105b'. FIG. 4b shows a disassembled view of one independent electrode sensor 105b' of the flexible multi-electrode sensing device 105b in FIG. 4a, and FIG. 4c shows a top view of one independent electrode sensor 105b' of the flexible multi-electrode sensing device 105b in FIG. 4a. The electrode sensor 105b' may comprise a flexible substrate 401, a sensing membrane 403 and a conductive wire 405, wherein the conductive wire 405 is on the flexible substrate 401, in contact with the sensing membrane 403, and connects to the multi-channel fixture 107. The flexible substrate 401 may comprise a polyethyleneterephthalate substate. The sensing membrane 403 is on the flexible substrate 401, and may comprise a ruthenium dioxide sensing membrane. In one embodiment, the sensing membrane 403 may be circular shaped with a diameter of 2.5 mm. The ruthenium dioxide sensing membrane may be deposited on the flexible substrate 401 by a radio frequency sputtering system. A material of the conductive wire 405 may comprise sliver paste, and the conductive wire 405 may be formed by a screen-print process.

In another embodiment, the independent electrode sensor 105b' may further comprise a growable layer 407 on the flexible substrate 401, wherein the sensing membrane 403 and conductive wire 405 are on the growable layer 407. A material of the growable layer 407 may comprise epoxy resin. Furthermore, in another embodiment, the independent electrode sensor 105b' may further comprise a insulating layer 409 on the sensing membrane 403 and the conductive wire 405, wherein the insulating layer 409 has a opening 411 for exposing a part of the sensing membrane 403, which forms a sensing window 411a. A material of the insulating layer 409 may comprise epoxy resin. In one embodiment, the opening may be circular shaped with a diameter of 2.0 mm.

In one embodiment, the independent electrode sensor 105b' has various complex layers on the flexible substrate 401, and the complex layers may comprise epoxy resin/ruthenium dioxide 4093, epoxy resin/sliver paste 4095 and epoxy resin/sliver paste/ruthenium dioxide 40953.

Figure 5A:
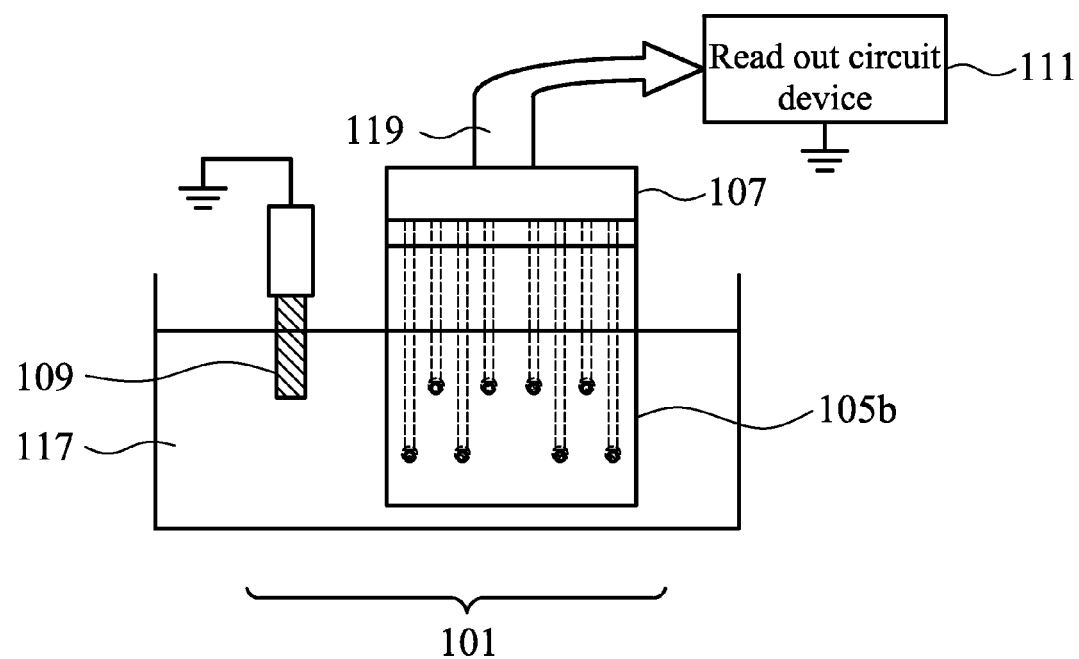
FIG. 5a shows an embodiment of the multi-electrode measuring system of the invention.
Figure 5B:
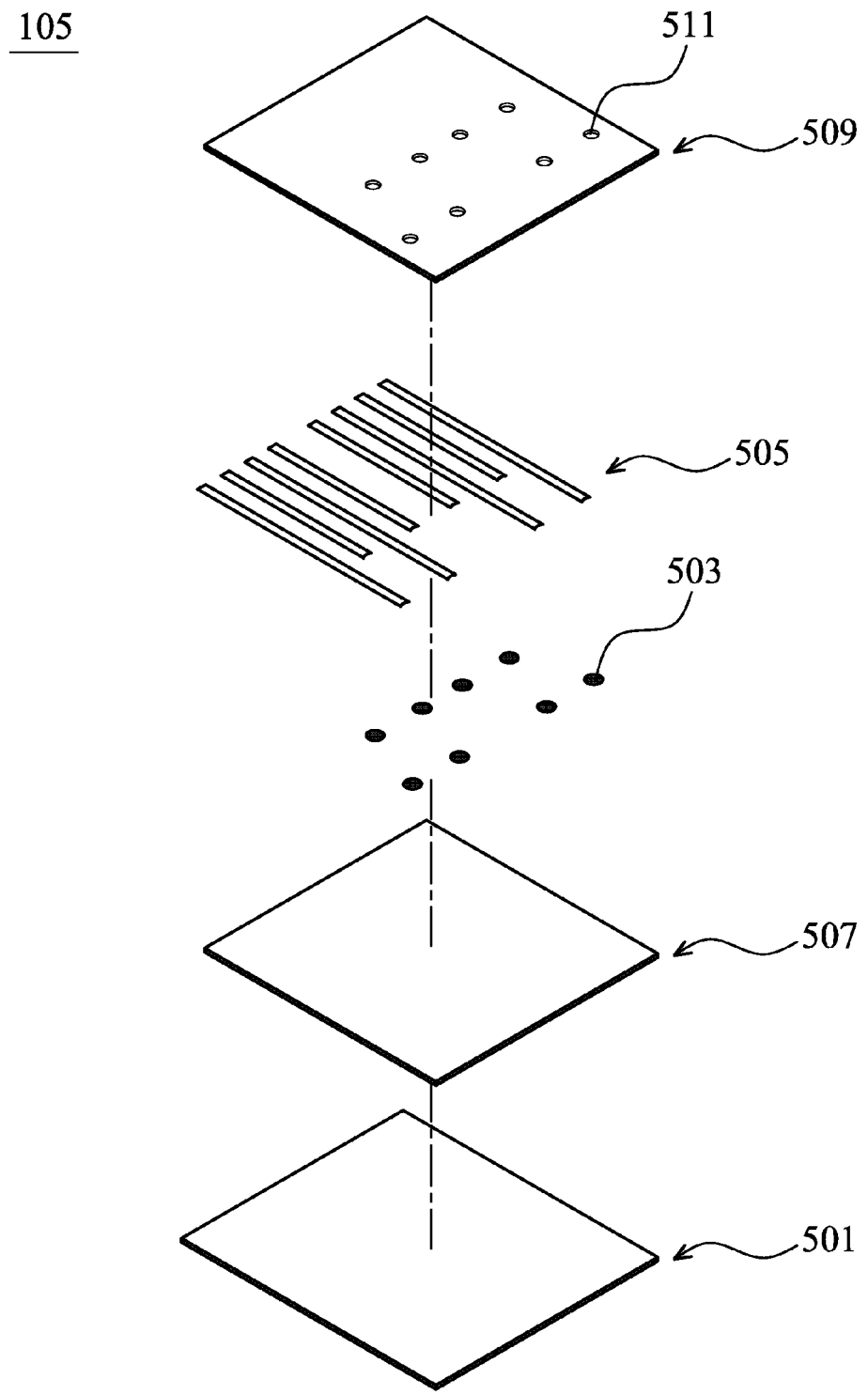
Figure 5C:
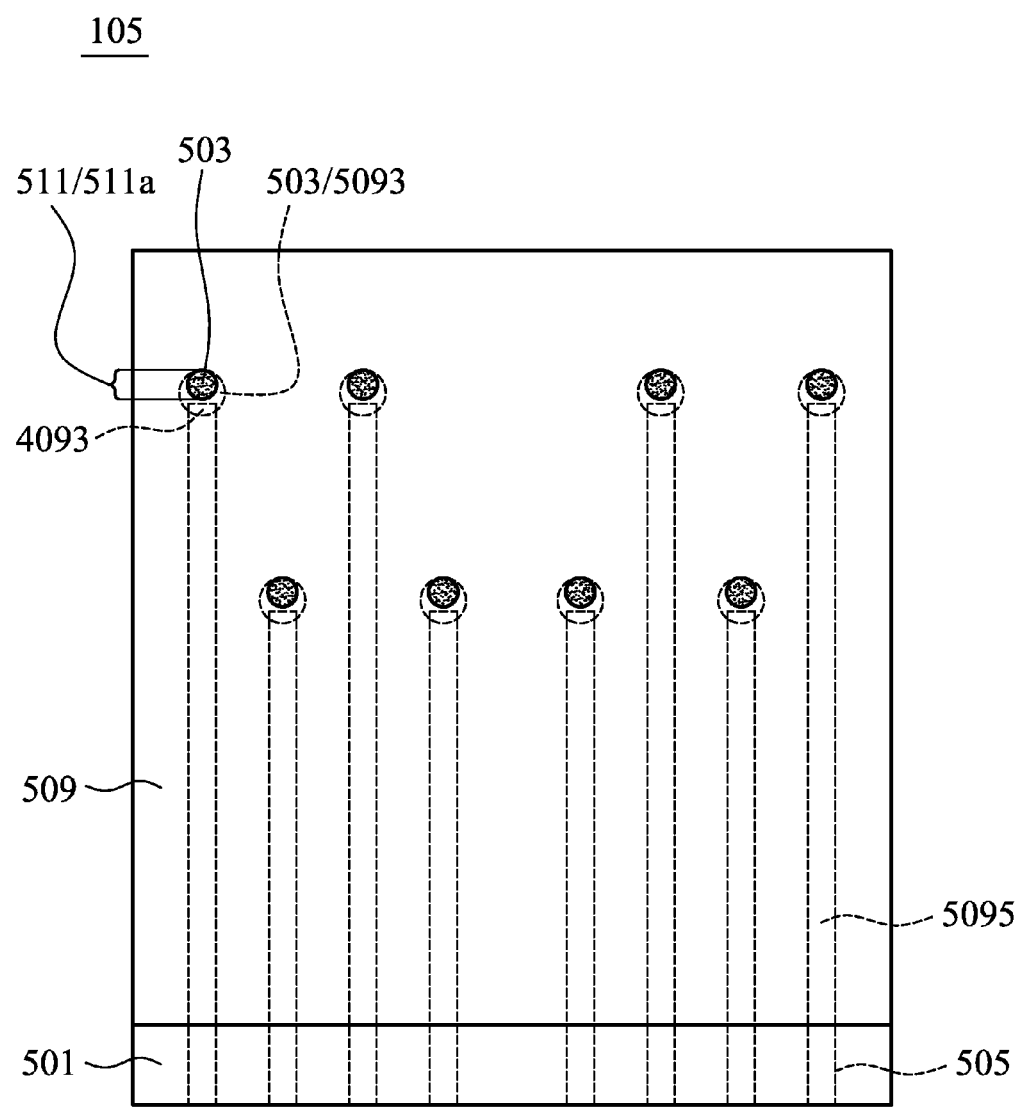

FIG. 5a shows an embodiment of the multi-electrode measuring system of the invention 500. The multi-electrode measuring system 500 has another embodiment of a flexible multi-electrode sensing device 105b. FIG. 5b shows a disassembled view of the flexible multi-electrode sensing device 105b in FIG. 5a, and FIG. 5c shows a top view of the flexible multi-electrode sensing device 105b in FIG. 5a. The flexible multi-electrode sensing device 105b may comprise a flexible substrate 501, a plurality of sensing membranes 503 and a plurality of conductive wires 505, wherein the plurality of conductive wires 505 is on the flexible substrate 501, in contact with the plurality of sensing membranes 503, and connects to the multi-channel fixture 107, respectively. The flexible substrate 501 may comprise a polyethyleneterephthalate substate. The sensing membrane 503 is on the flexible substrate 501, and may comprise a ruthenium dioxide sensing membrane. In one embodiment, the sensing membrane 503 may be circular shaped with a diameter of 2.5 mm. The ruthenium dioxide sensing membrane may be deposited on the flexible substrate 501 by a radio frequency sputtering system. A material of the conductive wire 505 may comprise sliver paste, and the conductive wire 505 may be formed by a screen-print process.

In another embodiment, the flexible multi-electrode sensing device 105b may further comprise a growable layer 507 on the flexible substrate 501, wherein the plurality of sensing membranes 503 and the plurality of conductive wires 505 are on the growable layer 507. Furthermore, in another embodiment, the flexible multi-electrode sensing device 105b may further comprise an insulating layer 509 on the plurality of sensing membranes 503 and the plurality of conductive wires 505, wherein the insulating layer 509 has a plurality of openings 511 for exposing the plurality of sensing membranes 503, which forms a plurality of sensing windows 511a. A material of the insulating layer 509 may comprise epoxy resin. In one embodiment, the opening may be circular shaped with a diameter of 2.0 mm.

In one embodiment, the flexible multi-electrode sensing device 105b has various complex layers on the flexible substrate 501, and the complex layers may comprise epoxy resin/ruthenium dioxide 5093, epoxy resin/sliver paste 5095 and epoxy resin/sliver paste/ruthenium dioxide 50953.

Refer to FIG. 1 again. The back-end device 103 is an electronic device and may comprise a read out circuit device 111, a data acquisition device 113 and a signal processing device 115. The signal processing device 115 of the back-end device 103 is different from traditional instrumentation, and the signal processing device 115 controls the hardware devices by a program designed for measuring a sample solution, and thus the whole back-end device 103 may be used as a virtual instrumentation. The read out circuit device 111 is coupled to the multi-channel fixture 107 and the reference electrode 109 for receiving each original signal from each electrode of the multi-electrode sensing device and the reference electrode determining a sample solution 117. The data acquisition device 113 is coupled to the read out circuit device 111 for generating each digital signal. In one embodiment, the data acquisition device 113 may comprise a single converter which performs multi-sampling and quantifies each original signal and encodes that signal according to the binary system to generate each digital signal. In another embodiment, the data acquisition device 113 may comprise a plurality of converters for performing array sampling and quantify each original signal and encode that according to the binary system to generate each digital signal. The signal processing device 115 may be used as an operation process core of the virtual instrumentation, wherein the signal processing device 115 is coupled to the data acquisition device 113 for processing each digital signal. In one embodiment, the multi-channel fixture 107 and the read out circuit device 111 are coupled through a shielded transmission line 119. In one embodiment, the shielded transmission line 119 transmits singles by multiple line transmission.

Figure 6:
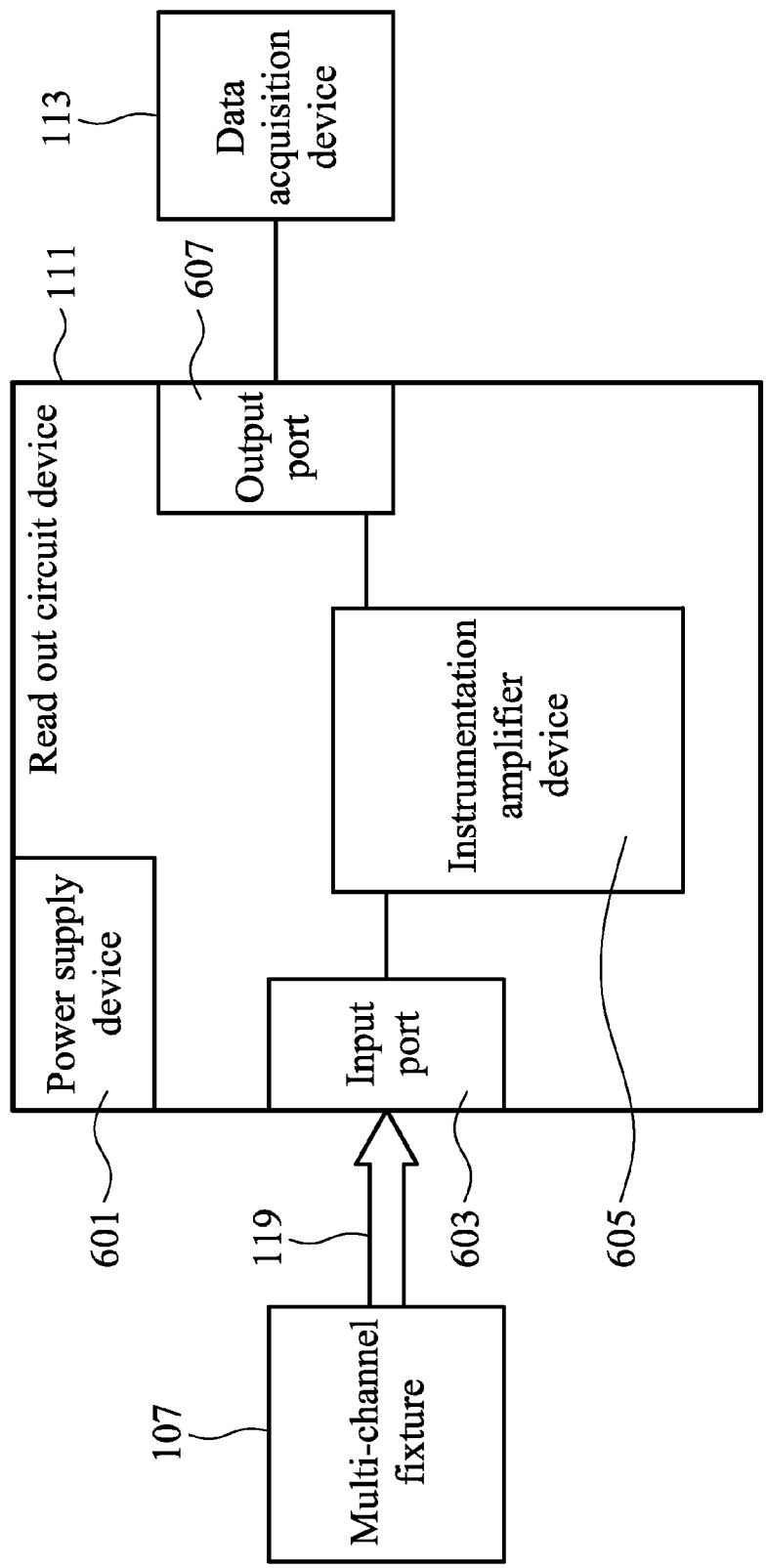
FIG. 6 shows a top view of the read out circuit device.

See FIG. 6. The read out circuit device 111 comprises a power supply device 601, an input port 603, an instrumentation amplifier device 605 and an output port 607, wherein the input port 603 is coupled to the multi-channel fixture 107 and the reference electrode 109, the instrumentation amplifier device 605 is couple to the input port 603 and the output port 607 is coupled to the instrumentation amplifier device 605 and the data acquisition device 113. The power supply device 601 is used for providing power to the input port 603, the instrumentation amplifier device 605 and the output port 607. In one embodiment, the power supply device may comprise a direct current dual power supply or direct current single-to-dual power supply. The instrumentation amplifier device may adopt a conventional instrumentation amplifier device, such as AD 620, AD 8231, etc. from Analog Device (AD), INA 121, INA 333 from Texas Instruments (TI), LT 1167, LTC 2053 from Linear Technology (LT) and the similar devices thereof. The input port receives each original signal from each electrode of the multi-electrode sensing device and the reference electrode determining a sample solution 117, respectively and transmits that to the instrumentation amplifier device. The instrumentation amplifier device amplifies the signals mentioned above and transmits them to the output port, and the output port transmits the amplified singles to the data acquisition device 113.

The data acquisition device 113 is used for converting the original signals (analog signals) into digital signals by processes of sampling, quantification, encoding, generation, etc. The data acquisition device 113 may be, such as commercial NI-USB 6210, NI-USB 6211, NI-PCI 6010 and the similar devices thereof, or may be a commercialized integrated circuit which is able to convert analog signals into digital signals, such as AD7810, AD7880 from Analog Device (AD), TLV1549, ADS7844 form Texas Instruments (TI) and LTC2309, LTC2356 from Linear Technology (LT), etc. The use of digital signals is an identical method for processing the signals. The analog signals are easily interfered with external noise and hard to be exercised in the digital operation and thus the digital single process may be used to remove the noise, recover the quality of the original signals, remove the signals from the real world or perform a difficult algorithm.

Frameworks for the signal processing device 115 processing each digital signal may comprise an acquisition framework, a digital filter framework, a display framework, a storage framework and an analysis framework, wherein these frameworks may be operated by a program, such as LabVIEW (Version 7.1) from National Instruments or a programmable software with similar functions. The acquisition framework dynamically receives sampling data from the data acquisition device, and makes the sampling data be in data array form (array sampling data). The digital filter framework calculates a series of the data of the array sampling from each electrode obtained from the acquisition framework to form a group of estimated direct current values. The display framework immediately displays the group of estimated direct current values on a display. The storage framework immediately saves the group of estimated direct current values in a memory unit. The analysis framework calculates the group of estimated direct current values imported from the memory unit by a particular algorithm and analyzes the sensitivity, linearity and stability of the multi-electrode sensing device.

The signal processing device 115 may comprise a personal computer, notebook computer, field programmable gate array or digital signal processor.

EXAMPLE

Multi-electrode Measuring System

The multi-electrode measuring system with a non-flexible multi-electrode sensing device as shown in FIG. 2a and the multi-electrode measuring system with a flexible multi-electrode sensing device as shown in FIG. 5a were used to determine phosphate buffers (pH 1-13), respectively.

The non-flexible multi-electrode sensing device and the flexible multi-electrode sensing device had 8 sensing windows, respectively.

The back-end device of the multi-electrode measuring system comprised a read out circuit device, a data acquisition device and a signal processing device.

Read Out Circuit Device

Figure 7:
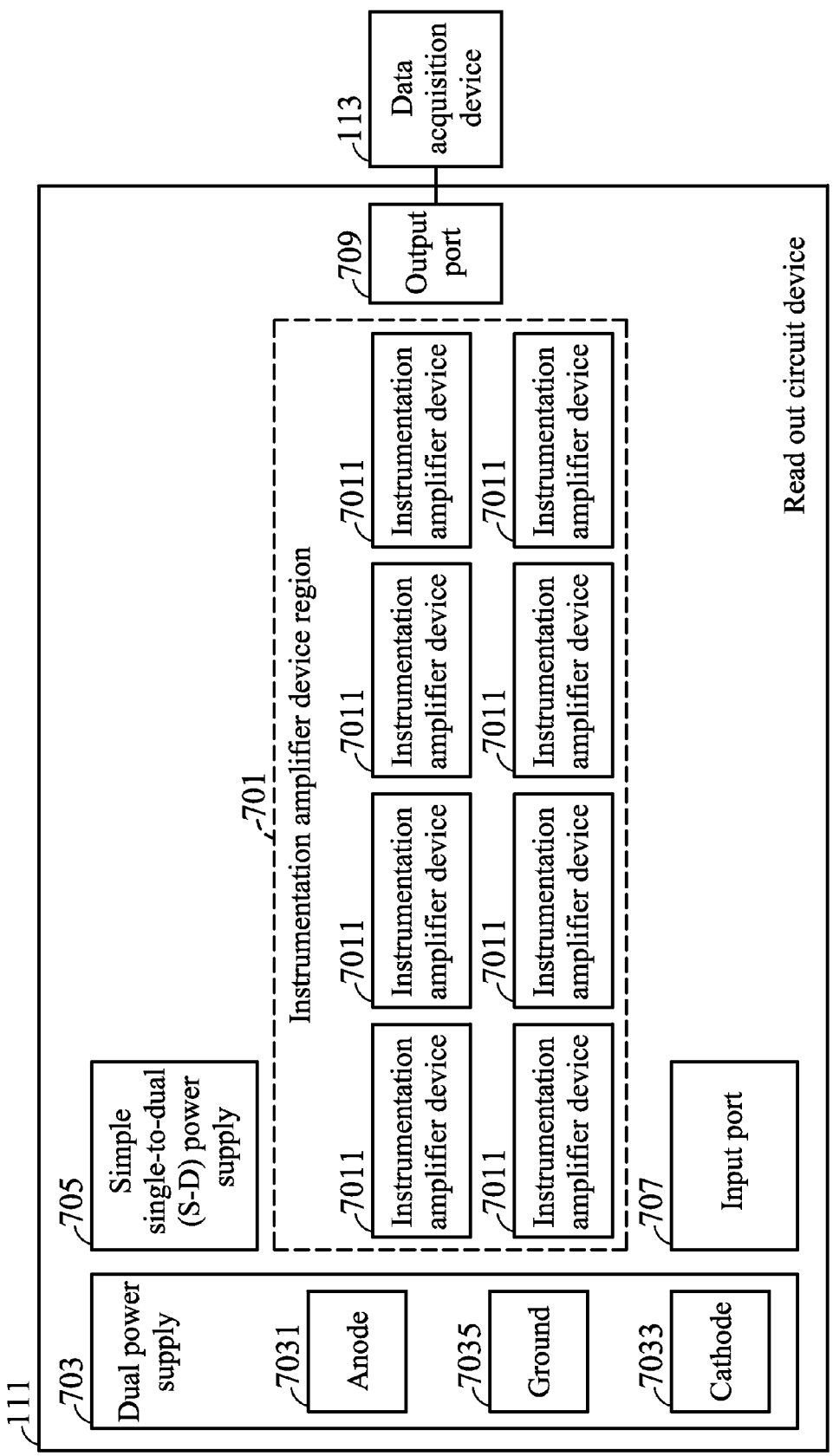
FIG. 7 shows the framework of the read out circuit device.

The framework of the read out circuit device was shown as FIG. 7. The read out circuit device comprised two types of power supplies comprising a direct current dual power supply device and a direct current single to dual power supply device, a set of input port/output port, and a set of instrumentation amplifier devices.

Each part of the read out circuit device will be detailed in the following paragraphs.

(1) Instrumentation amplifier device region 701: Instrumentation amplifier device 7011 was the typical voltage amplifier providing a high input impedance (the ideal case is infinite) to load-in the input signals from the front-end circuit/system and a low output impedance (the ideal case is zero) to transmit the process signals to back-end circuit/system by an amplification with voltage (Av). In the instrumentation amplifier device, Av was set in '1' and the read-out circuit is made up with the voltage followers. Therefore, the read-out circuit mainly provides the function of impedance matching for the back-end device. For transmitting the original signal measured by the sensing device, instrumentation amplifier AD620 produced by Analog Device Inc. (U.S.) was used. AD620 was easy to use and possessed various functions such as setting gains range with one external resistor (gain range 1 to 10,000), low power (1.3 mA max. supply), wide power supply range (±2.3 V to ±18 V), low noise (0.28 μVp-p tested in 0.1 Hz to 10 Hz), 120 kHz bandwidth (G=100), low input offset voltage and input offset drift (50 μV max and 0.6 μV/° C. max., respectively), etc. In this invention, the amount of instrumentation amplifier devices 7011 was 8 corresponding to the electrodes.

(2) Power supply devices: Two types of methods are prepared to supply the power needed for the operation of instrumentation amplifier devices. One is directly using a commercial power supply (GW Instek PST-3201) providing a dual power supply 703 including anode (+Vcc) 7031, cathode (−Vss) 7033 and ground (G) 7035 (hint: c=circuit, and s=series). The other one is a simple single-to-dual (S-D) power supply 705 based on the time IC (Texas Instruments NE555) with an alternating current (AC) to direct current (DC) voltage converter (DC 6V, 150 mA) or a battery pack forming an astable multivibrator to obtain a continual square wave at 20 KHz for two capacitors (15-30 μF, 10-50 V) as the dual power supply. In addition, a power supply switch is used to exchange the power supply sources.

(3) Input port 707/output port 709: The input/output ports are prepared for 8 input/output transmission channels (8 electrodes) and one common ground, and the solution was to use the DuPont connector 2.54 9 pin. Additionally, the shielded transmission line was chosen to eliminate the environment noise and pulse, especially in higher frequencies.

Data Acquisition Device

Commercial NI-USB 6210 was selected as the data acquisition device to convert the analog signals into digital signals for use by procedures such as acquisition, quantification, encoding, generation, etc. NI-USB 6210 is a programmable data acquisition device and provides the control parameters such as sampling rate, sampling number, buffer size, etc. It offers 16 analog inputs, a 250 kS/s single-channel sampling rate, four programmable input ranges (±0.2 to ±10 V) per channel, etc.

Signal Processing Device

The signal processing device of the back-end device was different from a traditional instrument, and the signal processing device controlled the hardware devices using a program designed to reach the purpose of measurement, and thus the signal processing device in combination with the read out circuit device and the data acquisition device was called as a virtual instrumentation. In the signal processing device, the performed program design comprised an acquisition framework, a digital filter framework, a display framework, storage framework and an analysis framework. The measuring program designed in the invention is detailed in the following section.

(1) Acquisition and digital filter framework: The acquisition and digital filter framework were connected and performed by the software, LabVIEW, and the data acquisition device, and the related parameters of the designed programmable software were shown in the following.

1. Physical channels: select the input/output channels of the data acquisition device through DAQmx which is the hardware device driver of LabVIEW; in this example, the analog input ports were set in AI 0-AI 7.

2. Input range: decide the acquisition input range which will affect the acquisition resolution; in this example, input range was set from −1.5 V to 1.5 V.

3. Input terminal configuration: select the modes comprising Reference Single-End (RSE), Differential (DIFF), and Non-Referenced Single-End (NRSE), which decides the channel number; in this example, 'NRSE' was selected.

4. Samples per channel: decide the PC buffer size; in this example, the defined value '−1' was used.

5. Sample mode: the sampling method; in this example, the 'Continuous Samples' or 'Finite Samples' was selected to use.

6. Source: the generator mode of the sampling frequency; in this example, the defined value was selected to use the source on board.

7. Rate: the actual acquisition amount per second; in this example, 1-30 KS/s was selected for each channel of the 8 electrodes.

Furthermore, the operation of the software which was set according to the parameters of the invention comprised the selection of the instrument, measurement and interval time setting, the operational setting of the specific instrument, etc. The program required importing the acquisition data from the PC buffer to the computer. Finally, the data acquisition device was stopped by a stop program controlled by the software of the invention. When the measurement was completed, the device needed to stop functioning.

(2) Digital filter framework: The invention used a signal processing method, wherein a group of estimated direct current values was obtained by processing the imported acquisition data with the digital filter framework. The digital filter framework used a module of LabVIEW, the 'AC & DC Estimator' to execute the 'Harming Window' function and 'Mean' function to form a low-pass frequency digital filter. This module modified the information imported every acquisition cycle and obtained a group of estimated direct current values.

(3) Display and storage frameworks: The display and storage functions were executed after the software completed the acquisition and digital filter process to export a group of estimated direct current values. The storage frameworks would provide a dialogue window for an operator to decide the storage path and generate a blank storage electrical file in a form of Microsoft Office Excel electrical file (*.xls). Display procedures comprised a diagram of curves displaying write-in data. The diagram of curves displaying procedures utilized an object of 'Waveform Chart' which was able to record and display the generated DC values; the data writing-in procedure wrote the generated DC values in the existent Microsoft Office Excel electrical file (*.xls). After a series of writing-in procedure was completed, a close procedure was needed for the frameworks to terminate the connection between the framework and the Excel electrical file. The frameworks would retain the saving path and Excel file name, and then automatically execute and generate the completed measurement curve in the portable network graphics form, '*.png' form.

Analysis framework: After the measurement was completed, an Excel electrical file and diagram of curves of the measurement were obtained. The concrete analysis method of the invention comprised importing electrical files of the measurement to the analysis framework to execute the relative algorithm calculation.

Figure 8:
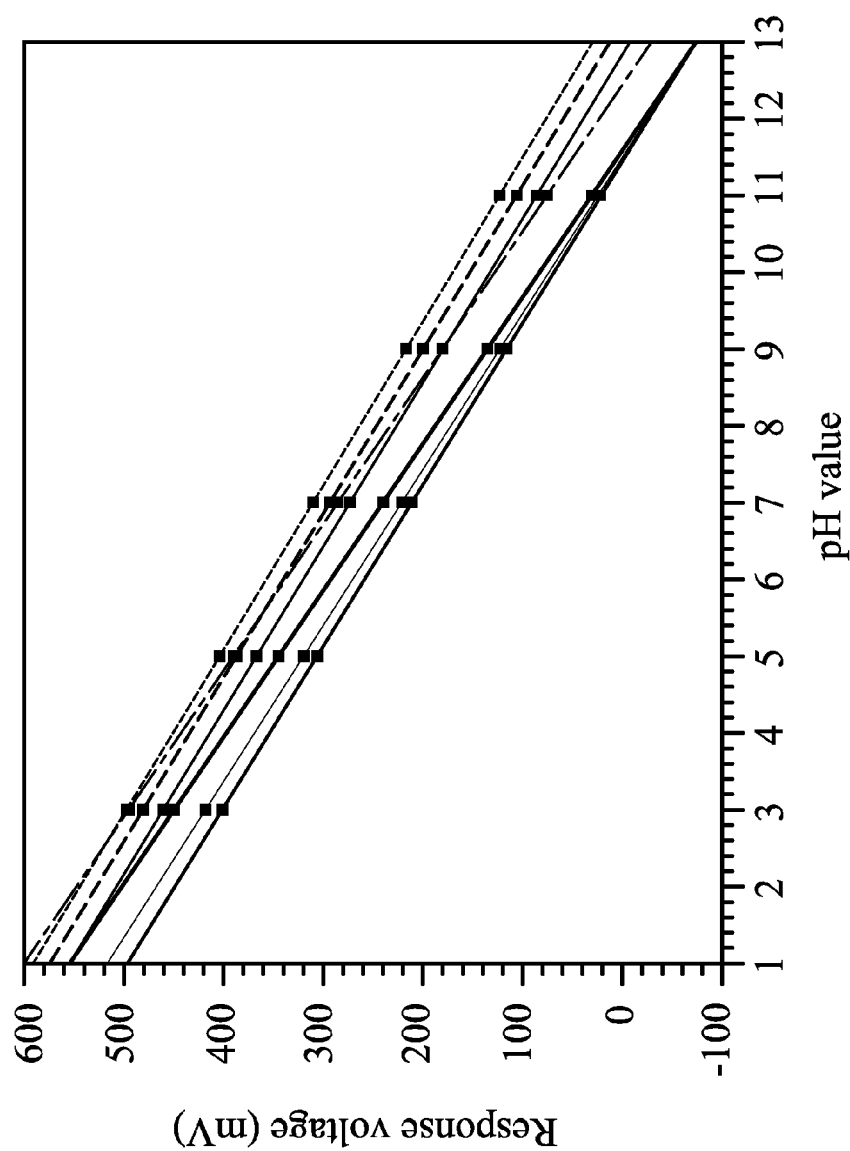
FIG. 8 shows sensitivity and linearity measured and analyzed by each flexible electrode in one embodiment.
Figure 9:
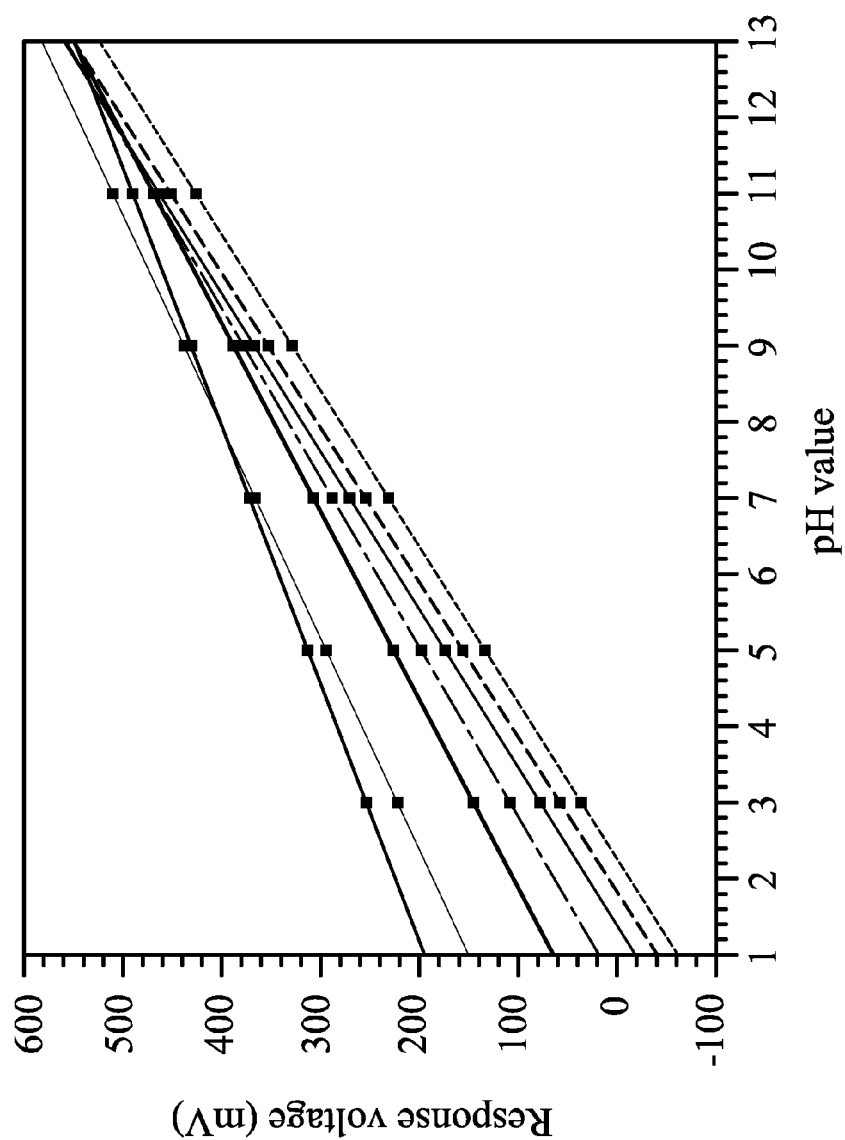
FIG. 9 shows sensitivity and linearity measured and analyzed by each non-flexible electrode in one embodiment.

Comparison of the non-flexible multi-electrode sensing device with the flexible multi-electrode sensing device After the multi-electrode measuring system with the non-flexible multi-electrode sensing device was used to determine the phosphate buffers (pH 1-13), the graph of property analysis for the non-flexible multi-electrode sensing device was obtained and shown as FIG. 8. FIG. 8 shows the sensitivity and linearity of each non-flexible electrode. After the multi-electrode measuring system with the flexible multi-electrode sensing device was used to determine the phosphate buffers (pH 1-13), the graph of property analysis for the flexible multi-electrode sensing device was obtained and shown as FIG. 9. FIG. 9 shows the sensitivity and linearity of each flexible electrode. According to FIG. 8 and FIG. 9, it was understood that the sensitivity and linearity of the flexible multi-electrode sensing devices were batter than those of the non-flexible multi-electrode sensing devices.

Comparison Experiment

Figure 10:
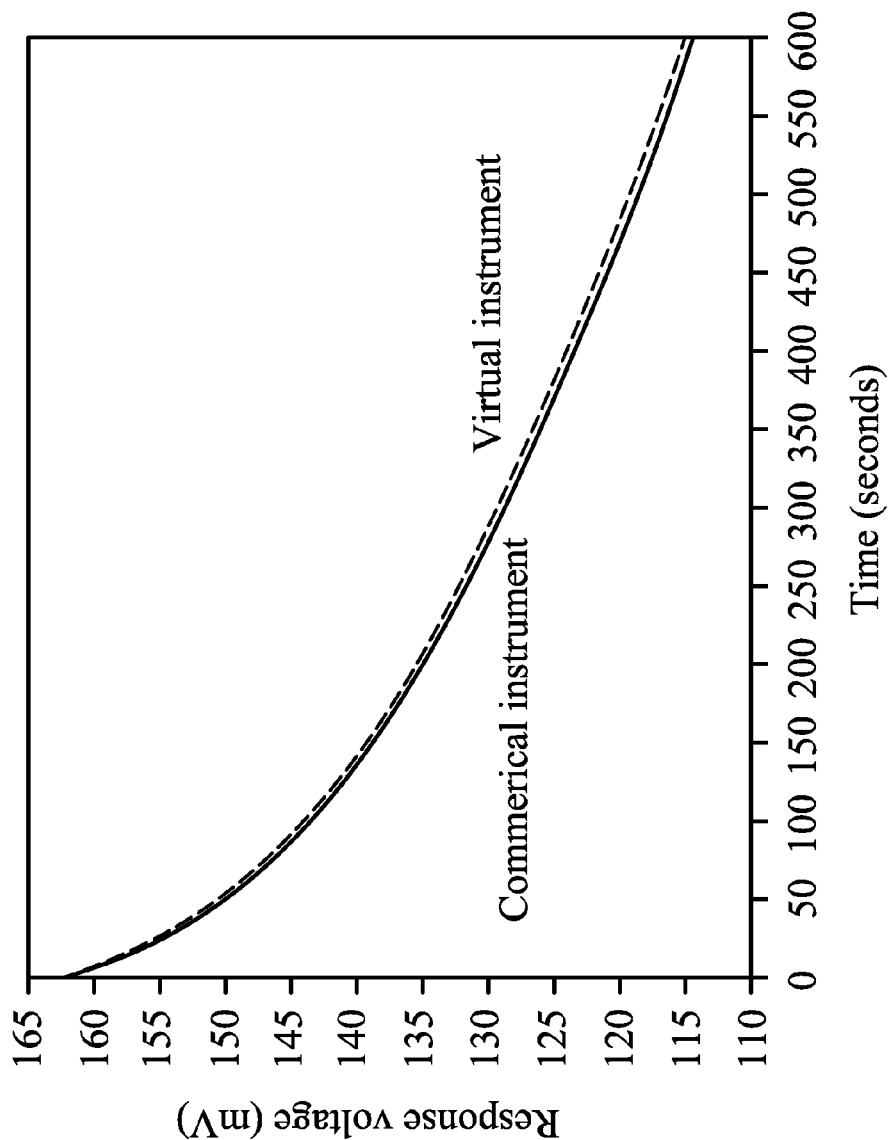
FIG. 10 shows a synchronous measurement comparison of the virtual instrumentation and the multimeter synchronous measurement comparison of virtual instrumentation and multimeter in the source of the $RuO_2$ electrode immersing in phosphate buffer saline solution (pH 7).

For proving the feasibility of the designed measurement system of the invention, an experiment was designed for comparison. In the same environment parameters (e.g. temperature, pressure, illumination, etc.), a commercial multimeter (HP 34401A) and the designed virtual instrumentation were used to detect response voltages from two types of sources, a direct current power supply output 50 mV and an $RuO_2$ sensing electrode in a pH 7 solution, respectively. The approach is just to increase an acquisition API of HP 34401A for parallel process using the error line when the referential virtual instrumentation software architecture (VISA) session is completed. After the detections of the direct current power supply and the $RuO_2$ electrode immersed in phosphate buffer saline solution (pH 7), the analysis results were tabulated and are shown in Table 1. The synchronous measurement comparison of the virtual instrumentation and the multimeter (HP 34401A) in the source of the $RuO_2$ sensing electrode immersed in the phosphate buffer saline solution (pH 7) is shown in FIG. 10. According to Table 1, it was understood that the results from the multimeter and of the virtual instrumentation had similar standard deviations (S.D.) both in the source of direct current power supply and EIS system. This indicates that the variability of the multimeter and that of the virtual instrumentation were similar. The amount of maximum error (M.E.) between the multimeter and virtual instrumentation in the same source (direct current power supply or the $RuO_2$ electrode immersed in phosphate buffer saline solution (pH 7)) is less than 1 mv and it specified that the measured direct current voltage in the virtual instrumentation is closer to that in the multimeter. According to the results, the feasibility of the designed measurement system is verified and reliable.

TABLE 1

Compared analysis result between the commercial instrument and the virtual instrumentation.

| | Source | | | |
|---|---|---|---|---|
| | Direct current power supply (mV) | | Sensing electrode (mv) | |
| | Device | | | |
| | Multimeter | Virtual instrumentation | Multimeter | Virtual instrumentation |
| Mean | 48.362 | 48.683 | 130.986 | 131.399 |
| S.D. | 0.026 | 0.021 | 11.917 | 11.913 |
| M.E. | | 0.639 | | 0.345 |

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A multi-electrode measuring system, comprising:
    a front end device which is a sensing device comprising:
        a multi-electrode sensing device having a plurality of electrodes;
        a multi-channel fixture coupled to the multi-electrode sensing device; and
        a reference electrode; and
    a back-end device as a virtual instrumentation which is an electronic device comprising:
        a read out circuit device coupled to the multi-channel fixture and the reference electrode for receiving each original signal from each electrode of the multi-electrode sensing device and the reference electrode determining a sample solution;
        a data acquisition device coupled to the read out circuit device for digitizing each original signal to form a digital signal and for array sampling; and
        a signal processing device coupled to the data acquisition device for processing each digital signal, wherein frameworks for the signal processing device processing each digital signal comprises:
an acquisition framework for dynamically receiving data of the array sampling of the digital signal of each electrode from the data acquisition device;
a digital filter framework for calculating a series of the data of the array sampling from each electrode obtained from the acquisition framework to from a group of estimated direct current values;
a display framework for immediately displaying the group of estimated direct current values on a display;
a storage framework for immediately saving the group of estimated direct current values in a memory unit; and
an analysis framework for calculating the group of estimated direct current values converged therein via the storage framework by a particular algorithm.

2. The multi-electrode measuring system as claimed in claim 1, wherein the multi-channel fixture and the read out circuit device are coupled through a shielded transmission line.

3. The multi-electrode measuring system as claimed in claim 1, wherein the multi-electrode sensing device comprises a non-flexible multi-electrode sensing device or a flexible multi-electrode sensing device.

4. The multi-electrode measuring system as claimed in claim 3, wherein the non-flexible multi-electrode sensing device comprises a plurality of independent electrode sensors, each electrode sensor comprising:
a non-flexible substrate;
a sensing membrane on the non-flexible substrate; and
a conductive wire extended from the sensing membrane, wherein the conductive wire connects to the multi-channel fixture.

5. The multi-electrode measuring system as claimed in claim 4, wherein the non-flexible substrate comprises a silicon substrate.

6. The multi-electrode measuring system as claimed in claim 4, wherein the sensing membrane comprises a ruthenium dioxide sensing membrane.

7. The multi-electrode measuring system as claimed in claim 6, wherein the ruthenium dioxide sensing membrane is deposited on the non-flexible substrate by a radio frequency sputtering system.

8. The multi-electrode measuring system as claimed in claim 4, wherein the electrode sensor further comprises a plastic shell for covering the conductive wire.

9. The multi-electrode measuring system as claimed in claim 4, wherein the electrode sensor further comprises an insulating package layer for packing the non-flexible substrate and the sensing membrane, wherein the insulating package layer has a opening for exposing a part of the sensing membrane.

10. The multi-electrode measuring system as claimed in claim 9, wherein a material of the insulating package layer comprises epoxy resin.

11. The multi-electrode measuring system as claimed in claim 3, wherein the non-flexible multi-electrode sensing device comprises:
a non-flexible substrate;
a plurality of sensing membranes on the non-flexible substrate; and
a plurality of conductive wires extended from the plurality of sensing membrane, wherein the plurality of conductive wires connects to the multi-channel fixture, respectively.

12. The multi-electrode measuring system as claimed in claim 11, wherein the non-flexible substrate comprises a silicon substrate.

13. The multi-electrode measuring system as claimed in claim 11, wherein the sensing membrane comprises a ruthenium dioxide sensing membrane.

14. The multi-electrode measuring system as claimed in claim 13, wherein the ruthenium dioxide sensing membrane is deposited on the non-flexible substrate by a radio frequency sputtering system.

15. The multi-electrode measuring system as claimed in claim 11, wherein the non-flexible multi-electrode sensing device further comprises a plastic shell for covering the conductive wire.

16. The multi-electrode measuring system as claimed in claim 11, wherein the non-flexible multi-electrode sensing device further comprises an insulating package layer for packing the non-flexible substrate and the plurality of sensing membranes, wherein the insulating package layer has a plurality of openings for exposing a part of each of the plurality of sensing membranes, respectively.

17. The multi-electrode measuring system as claimed in claim 16, wherein a material of the insulating package layer comprises epoxy resin.

18. The multi-electrode measuring system as claimed in claim 3, wherein the flexible multi-electrode sensing device comprises a plurality of independent electrode sensors, each electrode sensor comprising:
a flexible substrate;
a sensing membrane on the flexible substrate; and
a conductive wire on the flexible substrate in contact with the sensing membrane and connecting to the multi-channel fixture.

19. The multi-electrode measuring system as claimed in claim 18, wherein the flexible substrate comprises a polyethyleneterephthalate substate.

20. The multi-electrode measuring system as claimed in claim 18, wherein the sensing membrane comprises a ruthenium dioxide sensing membrane.

21. The multi-electrode measuring system as claimed in claim 20, wherein the ruthenium dioxide sensing membrane is deposited on the flexible substrate by a radio frequency sputtering system.

22. The multi-electrode measuring system as claimed in claim 18, wherein a material of the conductive wire comprises a silver paste.

23. The multi-electrode measuring system as claimed in claim 18, wherein the conductive wire is formed by a screen-print process.

24. The multi-electrode measuring system as claimed in claim 18, wherein the electrode sensor further comprises a growable layer on the flexible substrate, wherein the sensing membrane and conductive wire are situated on the growable layer.

25. The multi-electrode measuring system as claimed in claim 24, wherein a material of the growable layer comprises epoxy resin.

26. The multi-electrode measuring system as claimed in claim 18, wherein the electrode sensor further comprises an insulating layer on the sensing membrane and the conductive wire, wherein the insulating layer has an opening for exposing the sensing membrane.

27. The multi-electrode measuring system as claimed in claim 26, wherein a material of the insulating layer comprises epoxy resin.

28. The multi-electrode measuring system as claimed in claim 3, wherein the flexible multi-electrode sensing device comprises:
a flexible substrate;
a plurality of sensing membranes on the flexible substrate; and
a plurality of conductive wires in contact with the plurality of sensing membranes and connecting to the multi-channel fixture, respectively.

29. The multi-electrode measuring system as claimed in claim 28, wherein the flexible substrate comprises a polyethyleneterephthalate substrate.

30. The multi-electrode measuring system as claimed in claim 28, wherein the sensing membrane comprises a ruthenium dioxide sensing membrane.

31. The multi-electrode measuring system as claimed in claim 28, wherein the ruthenium dioxide sensing membrane is deposited on the flexible substrate by a radio frequency sputtering system.

32. The multi-electrode measuring system as claimed in claim 28, wherein a material of the conductive wire comprises a silver paste.

33. The multi-electrode measuring system as claimed in claim 28, wherein the conductive wire is formed by a screen-print process.

34. The multi-electrode measuring system as claimed in claim 28, wherein the flexible multi-electrode sensing device further comprises a growable layer on the flexible substrate, wherein the plurality of sensing membranes and the plurality of conductive wires are situated on the growable layer.

35. The multi-electrode measuring system as claimed in claim 34, wherein a material of the growable layer comprises epoxy resin.

36. The multi-electrode measuring system as claimed in claim 28, wherein the flexible multi-electrode sensing device further comprises an insulating layer on the plurality of sensing membranes and the plurality of conductive wires, wherein the insulating layer has a plurality of openings for exposing the plurality of sensing membrane, respectively.

37. The multi-electrode measuring system as claimed in claim 36, wherein a material of the insulating layer comprises epoxy resin.

38. The multi-electrode measuring system as claimed in claim 1, wherein the reference electrode comprises an Ag/AgCl reference electrode.

39. The multi-electrode measuring system as claimed in claim 1, wherein the read out circuit device comprises:
a power supply device;
an input port coupled to the multi-channel fixture and the reference electrode;
an instrumentation amplifier device coupled to the input port; and
an output port coupled to the instrumentation amplifier device.

40. The multi-electrode measuring system as claimed in claim 39, wherein the power supply device comprises a direct current dual power supply or direct current single-to-dual power supply.

41. The multi-electrode measuring system as claimed in claim 1, wherein the data acquisition device comprises a single converter for performing a multiple sampling.

42. The multi-electrode measuring system as claimed in claim 1, wherein the data acquisition device comprises a plurality of converters for performing the array sampling.

43. The multi-electrode measuring system as claimed in claim 1, wherein the signal processing device comprises a personal computer, notebook computer, field programmable gate array or digital signal processor.

\* \* \* \* \*